United States Patent
Avnery (10) Patent No.: US 7,759,661 B2
(45) Date of Patent: Jul. 20, 2010

(54) ELECTRON BEAM EMITTER FOR STERILIZING CONTAINERS

(75) Inventor: Tzvi Avnery, Winchester, MA (US)

(73) Assignee: Advanced Electron Beams, Inc., Wilmington, MA (US)

(*) Notice: Subject to any disclaimer, the term of this patent is extended or adjusted under 35 U.S.C. 154(b) by 354 days.

(21) Appl. No.: 11/706,075

(22) Filed: Feb. 13, 2007

(65) Prior Publication Data

US 2008/0073549 A1    Mar. 27, 2008

Related U.S. Application Data

(60) Provisional application No. 60/773,047, filed on Feb. 14, 2006.

(51) Int. Cl.
*G21G 1/04* (2006.01)
*G21K 5/02* (2006.01)
*A61L 2/08* (2006.01)

(52) U.S. Cl. .............. 250/493.1; 250/492.1; 250/492.3; 422/23

(58) Field of Classification Search .............. 250/492.3, 250/492.1, 493.1, 494.1, 423 R, 491.1, 396 R, 250/397; 422/1, 21, 22, 23, 24, 7, 20; 204/157.15, 204/164, 157.44, 157.63, 163; 315/111.01, 315/111.81, 111.91
See application file for complete search history.

(56) References Cited

U.S. PATENT DOCUMENTS

| | | | |
|---|---|---|---|
| 2,602,751 A | 7/1952 | Robinson | |
| 3,383,163 A | 5/1968 | Menashi | |
| 3,621,327 A | 11/1971 | Hashmi | |
| 3,780,308 A | 12/1973 | Nablo | |
| 3,942,017 A * | 3/1976 | Uehara et al. | 250/492.3 |
| 4,652,763 A | 3/1987 | Nablo | |
| 4,983,849 A * | 1/1991 | Thompson et al. | 250/492.3 |
| 5,011,660 A | 4/1991 | Arena | |
| 5,422,068 A | 6/1995 | Shalaby et al. | |
| 5,489,783 A | 2/1996 | Kristiansson | |
| 5,512,244 A | 4/1996 | Griffiths et al. | |
| 5,730,933 A | 3/1998 | Peterson | |
| 5,811,943 A * | 9/1998 | Mishin et al. | 315/505 |
| 5,843,374 A * | 12/1998 | Sizer et al. | 422/24 |
| 6,139,796 A | 10/2000 | Kristiansson et al. | |
| 6,221,216 B1 * | 4/2001 | Nablo et al. | 204/157.15 |
| 6,348,241 B2 | 2/2002 | Ronge et al. | |
| 6,667,007 B1 * | 12/2003 | Schmidt | 422/22 |

(Continued)

FOREIGN PATENT DOCUMENTS

DE    10 10 201 B1    6/1957

(Continued)

*Primary Examiner*—David A Vanore
*Assistant Examiner*—Nicole Ippolito Rausch
(74) *Attorney, Agent, or Firm*—Hamilton, Brook, Smith & Reynolds, P.C.

(57) ABSTRACT

An electron beam emitter including a vacuum chamber having a width. An electron generator can be positioned within the vacuum chamber for generating electrons. An elongate nozzle can extend from the vacuum chamber along a longitudinal axis and have an exit window at a distal end of the nozzle. The nozzle can have a width that is less than the width of the vacuum chamber. The electron generator can be shaped and dimensioned, and positioned with the vacuum chamber to form and direct a narrow electron beam that enters and travels through the nozzle, and exits out the exit window.

30 Claims, 5 Drawing Sheets

U.S. PATENT DOCUMENTS

| | | | |
|---|---|---|---|
| 2002/0088948 A1* | 7/2002 | Avnery | 250/492.3 |
| 2002/0182101 A1 | 12/2002 | Koulik et al. | |
| 2003/0193033 A1* | 10/2003 | McIntyre | 250/492.3 |
| 2004/0047762 A1 | 3/2004 | Masaoka et al. | |
| 2004/0166426 A1* | 8/2004 | Tsukuda et al. | 430/30 |
| 2006/0192140 A1* | 8/2006 | Nablo et al. | 250/492.1 |
| 2006/0255288 A1* | 11/2006 | Petrov et al. | 250/398 |

FOREIGN PATENT DOCUMENTS

| | | |
|---|---|---|
| FR | 2 815 542 | 4/2002 |
| JP | 9150813 | 6/1997 |
| JP | 11248896 | 9/1999 |
| JP | 2002-104333 A | 4/2002 |
| JP | 2002-104334 | 4/2002 |
| JP | 2002-255124 | 9/2002 |
| JP | 2002-255125 | 9/2002 |
| JP | 2002-308229 | 10/2002 |
| JP | 2005-001712 | 1/2005 |
| JP | 2005-247427 | 9/2005 |
| WO | WO 01/04924 A1 | 1/2001 |

\* cited by examiner

ELECTRON BEAM EMITTER FOR STERILIZING CONTAINERS

RELATED APPLICATION

This application claims the benefit of U.S. Provisional Application No. 60/773,047, filed on Feb. 14, 2006. The entire teachings of the above application are incorporated herein by reference.

BACKGROUND

Electron beam emitters have been used for irradiating and sterilizing containers with electron beams. Typically, an electron beam emitter is positioned above the container and directs an electron beam downwardly into the container. However, when the container is a bottle with a narrow neck, adequate sterilization of the bottle becomes difficult. A narrow neck can block a large portion of the electron beam from entering the bottle.

SUMMARY

The present invention can provide an electron beam emitter including a vacuum chamber having a width. An electron generator can be positioned within the vacuum chamber for generating electrons. An elongate nozzle can extend from the vacuum chamber along a longitudinal axis and have an exit window at a distal end of the nozzle. The nozzle can have a width that is less than the width of the vacuum chamber. The electron generator can be shaped and dimensioned, and positioned within the vacuum chamber to form and direct a narrow electron beam that enters and travels through the nozzle, and exits out the exit window.

In particular embodiments, the nozzle can have a generally circular periphery, and a diameter. The vacuum chamber can have a generally circular periphery, and have a diameter that is larger than the diameter of the nozzle. The electron generator can have a housing with a diameter that is about the same as the diameter of the nozzle. The electron generator can be shaped and dimensioned, and positioned to form the electron beam with a converging portion that converges within the nozzle, followed by diverging portion that diverges within the nozzle before reaching the exit window. The electron beam can further diverge after exiting the exit window. The electron generator can include an electron generating filament that has a portion oriented generally longitudinally in line with the longitudinal axis of the nozzle. The nozzle can have a length, and a length to diameter ratio of at least about 3:1. The emitter can have a vacuum chamber diameter to nozzle diameter ratio of at least about 2:1.

The present invention can also provide a method of generating an electron beam, including generating electrons with an electron generator positioned within a vacuum chamber, the vacuum chamber having a width. An elongate nozzle can extend from the vacuum chamber along a longitudinal axis. The nozzle can have an exit window at a distal end of the nozzle. The nozzle can have a width that is less than the width of the vacuum chamber. The electron generator can be shaped and dimensioned, and positioned within the vacuum chamber to form and direct a narrow electron beam that enters and travels through the nozzle and exits out the exit window.

In particular embodiments, the nozzle can have a generally circular periphery, and a diameter. The vacuum chamber can have a generally circular periphery, and a diameter that is larger than the diameter of the nozzle. The electron generator can have a housing with a diameter that is about the same as the diameter of the nozzle. The electron generator can be shaped and dimensioned, and positioned to form the electron beam with a converging portion that converges within the nozzle, followed by a diverging portion that diverges within the nozzle before reaching the exit window. The electron beam can further diverge after exiting the exit window. The electron generator can include an electron generating filament. A portion of the filament can be oriented generally longitudinally in line with the longitudinal axis of the nozzle. The nozzle can have a length, and a length to diameter ratio of at least about 3:1. The vacuum chamber and the nozzle can have a vacuum chamber diameter to nozzle diameter ratio of at least about 2:1.

The present invention can also provide a method of irradiating an interior of a bottle, in which the bottle has a neck. Electrons can be generated with an electron generator positioned within a vacuum chamber, the vacuum chamber having a width. An elongate nozzle can extend from the vacuum chamber along a longitudinal axis. The nozzle can have an exit window at a distal end of the nozzle. The nozzle can have a width that is less than the width of the vacuum chamber. The electron generator can be shaped and dimensioned, and positioned within the vacuum chamber to form and direct a narrow electron beam that enters and travels through the nozzle, and exits out the exit window. The nozzle can be inserted through the neck of the bottle and irradiate the interior with the electron beam.

In particular embodiments, the elongate nozzle can have a generally circular periphery, and a diameter. The vacuum chamber can have a generally circular periphery, and a diameter that is larger than the diameter of the nozzle. The electron generator can have a housing with a diameter that is about the same as the diameter of the nozzle. The electron generator can be shaped and dimensioned, and positioned to form the electron beam with a converging portion that converges within the nozzle, followed by a diverging portion that diverges within the nozzle before reaching the exit window. The electron beam can further diverge after exiting the exit window. The electron generator can include a electron generating filament having a portion oriented generally longitudinally inline with the longitudinal axis of the nozzle. The nozzle can have a length, and a length to diameter ratio of at least about 3:1. The vacuum chamber and the nozzle can have a vacuum chamber diameter to nozzle diameter ratio of at least about 2:1. The bottle and the nozzle can be moved relative to each other during irradiation. The distribution of the electron beam within the interior of the bottle can be assisted with at least one electron directing member adjacent to the bottle. The interior of the bottle can have an ambient gaseous environment. The gaseous environment can be modified within the bottle.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION

Figure 1:
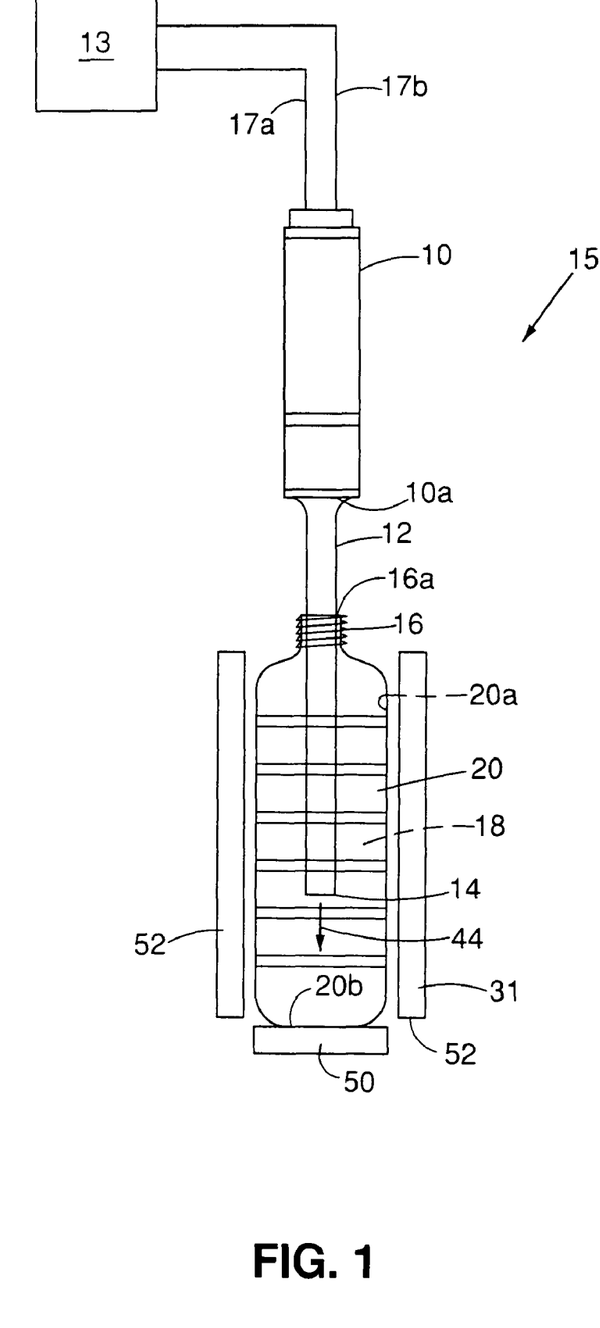
FIG. 1 is a side schematic view of an embodiment of a sterilization system.
Figure 2:
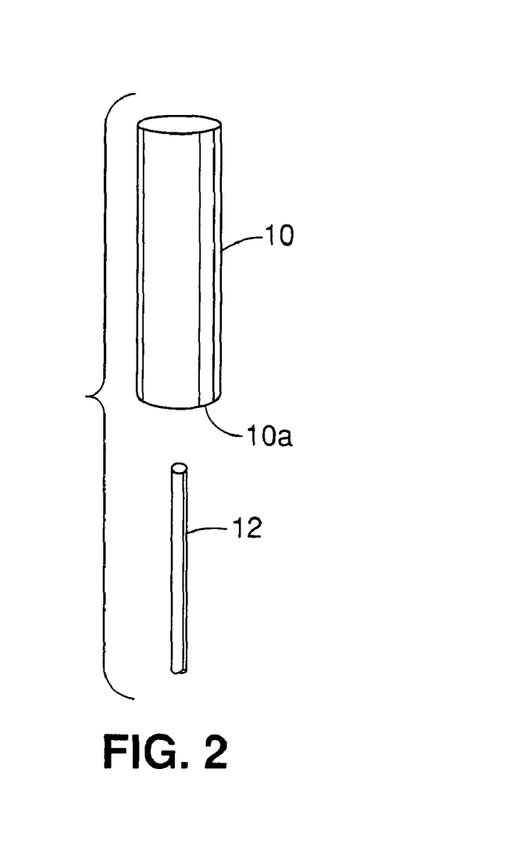
FIG. 2 is a perspective exploded view of an electron beam emitter having a nozzle.

A description of example embodiments follows. Referring to FIG. 1, sterilization system 15 can include an electron beam emitter 10 having a vacuum chamber 11. A pipe, conduit, tube or nozzle 12 (FIG. 2) can extend from, and be connected or secured and sealed to the axial end 10a of the vacuum chamber 11. An electron beam 44 can be emitted through the nozzle 12. The nozzle 12 can be narrow and elongate, allowing the nozzle 12 to be inserted into the opening 16a of a narrow neck 16 of a container such as a bottle 20, for irradiating the interior 18 of the bottle 20 with the electron beam 44 to irradiate, treat or sterilize surfaces in the interior 18. The vacuum chamber 11 can remain outside the bottle 20 while the nozzle 12 is inserted in the neck 16. Electrical power to electron beam emitter 10 can be provided by a power source 13 via lines 17a and 17b.

The interior 18 of the bottle 20 can be irradiated as the nozzle 12 is inserted and/or withdrawn from the bottle 20, or after insertion. The distance in which the nozzle 12 is inserted into the bottle 20 can depend upon the size of the bottle 20, including the height, width or diameter, as well as the intensity of the electron beam 44. Treatment or sterilization of the interior of the bottle 20 can be achieved by one or more of disabling, killing, destroying, vaporizing, oxidizing, altering, etc., microorganisms and biological substances within the interior 18 and on the interior surfaces 20a of the bottle 20. In addition, non-biological substances can be treated to neutralize, reduce or remove harmful effects.

Figure 3:
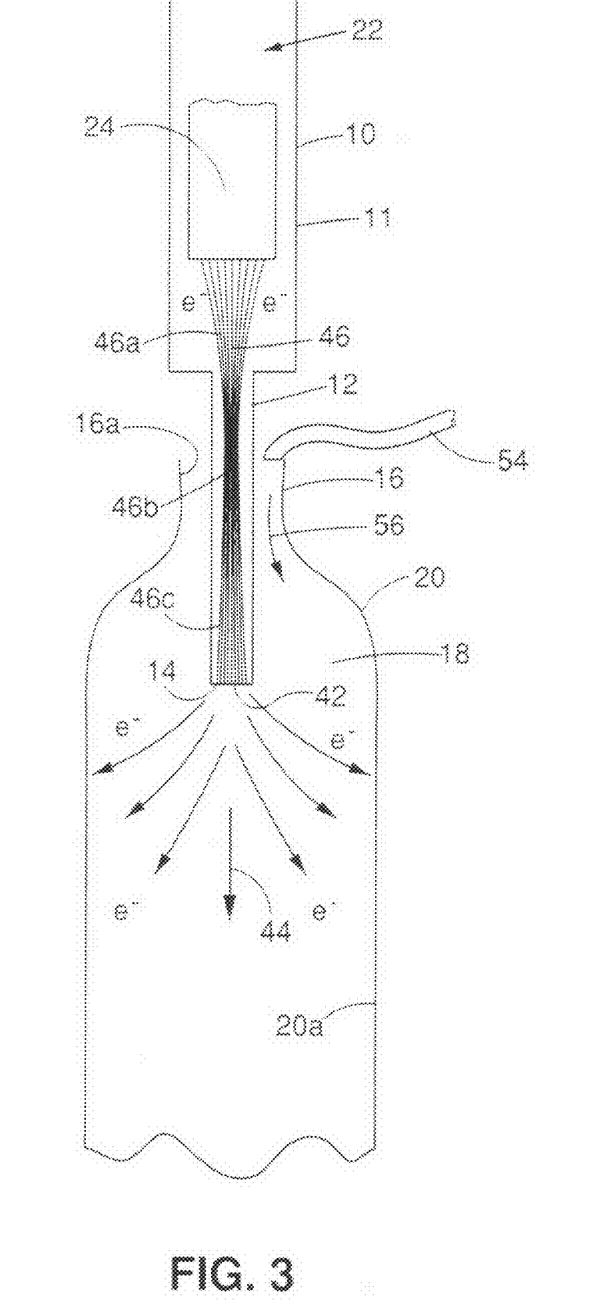
FIG. 3 is a side schematic view of a nozzle of an electron beam emitter inserted into a bottle.

The bottle 20 can be positioned on a support 50 which can move the bottle 20 up and down, or relative to the nozzle 12. If desired, the support 50 can also be rotated for rotating the bottle 20 to evenly irradiate the interior 18 of the bottle 20. Alternatively, the electron beam emitter 10 can be moved up and down, or relative to the bottle 20, and/or rotated. One or more electron shaping, spreading or directing plates or members 52 can be provided adjacent to the bottle 20 for distributing, shaping, spreading, directing or assisting electrons $e^-$ in the electron beam 44 (FIG. 3) to reach the interior surfaces 20a of the bottle 20 in a desired manner, or pattern or configuration, for treatment or sterilization. The electron directing members 52 can assist the distributing, shaping, spreading or directing of the electrons $e^-$ with magnetism, or electric potential or charge. One or more electron directing members 52 can be located at one or more locations laterally adjacent to the bottle 20, or alternatively, surround the exterior of the bottle 20 laterally circumferentially. In addition, the support 50 can also be used as a shaping, spreading or directing plate or member, for distributing, shaping, spreading directing, or assisting electrons $e^-$ to the bottom interior surface 20b of the bottle 20 in a desired manner, pattern or configuration. The support 50 can be provided with magnets, or electric potential or charge. The electron directing members 52 and the support 50 can receive power from power source 13.

If desired, a light gas 56 (FIG. 3) such as helium can be introduced into the bottle 20 by a nozzle or tube 54 to modify the ambient or existing gaseous environment and increase the range of the electron beam 44. In addition, the gas 56 can be used to form a plasma in conjunction with the electron beam 44, which can assist the treatment or sterilization process. Alternatively, nozzle or tube 54 can be a vacuum nozzle or tube for removing air from the bottle 20 to modify the gaseous environment, creating a vacuum or a partial vacuum. This can also increase the range of the electron beam 44 and assist in the treatment or sterilization process.

Figure 4:
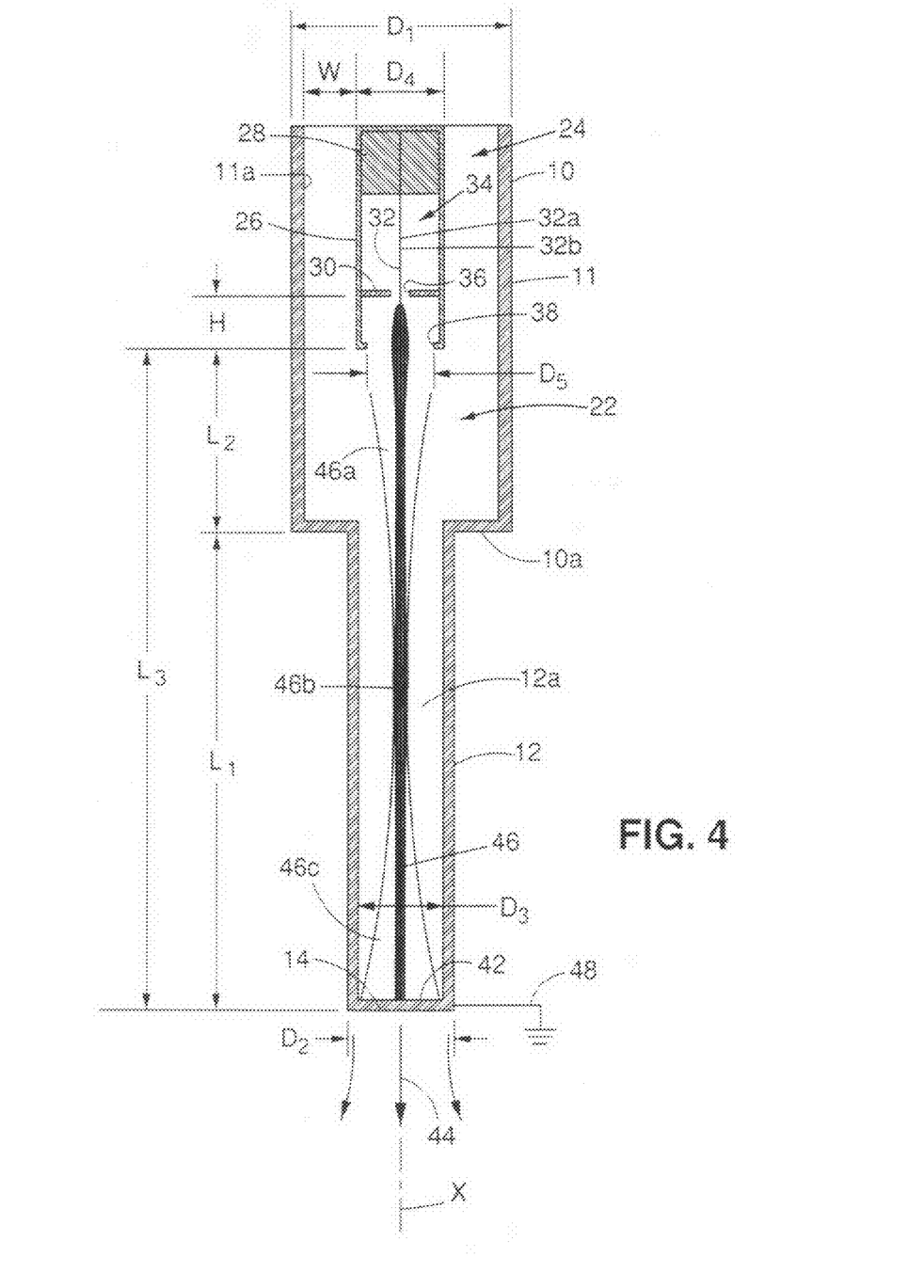
FIG. 4 is a side schematic view of a portion of an electron beam emitter with a nozzle.

Referring to FIGS. 3-6, vacuum chamber 11 of the electron beam emitter 10 can be generally cylindrical and elongate in shape with a width or diameter $D_1$ (FIG. 4). The nozzle 12 can also be generally cylindrical or tubular in shape with a length $L_1$, an outer width or diameter $D_2$, and an inner width or diameter $D_3$. The nozzle 12 can be inserted into small openings that would be too small to allow the insertion of an electron beam emitter 10 which did not have a narrow nozzle 12, and instead had an exit window 42 at the axial end 10a of the vacuum chamber 11. Having vacuum chamber 11 with a diameter $D_1$ that is larger than the diameter $D_2$ of the nozzle 12 can allow the electron beam emitter 10 to operate at higher power than if the electron beam emitter 10 were constructed to have a single small diameter of the same size as the nozzle 12. The vacuum chamber 11 and nozzle 12 can be joined together in a manner to have a permanent hermetically sealed vacuum therein.

Figure 5:
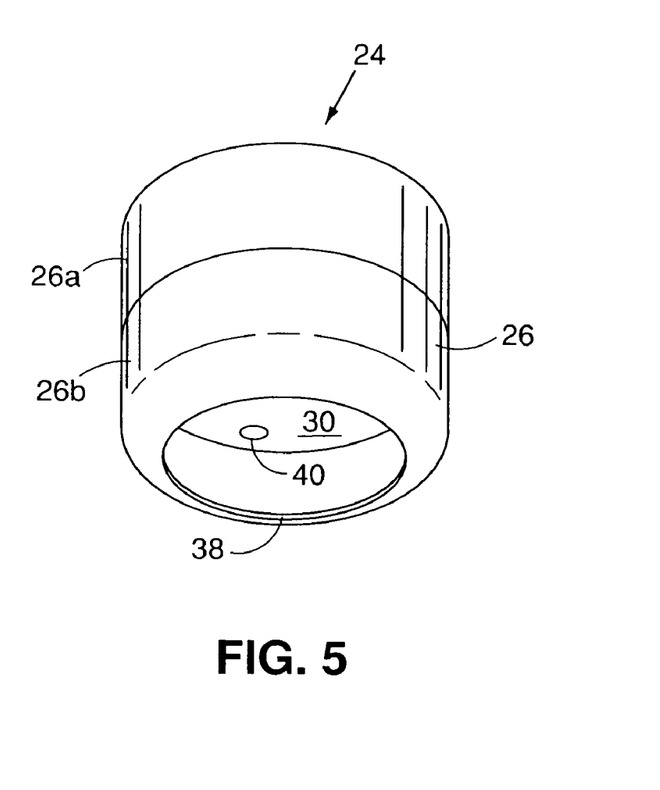
FIG. 5 is a perspective view of an electron beam gun or generator.
Figure 6:
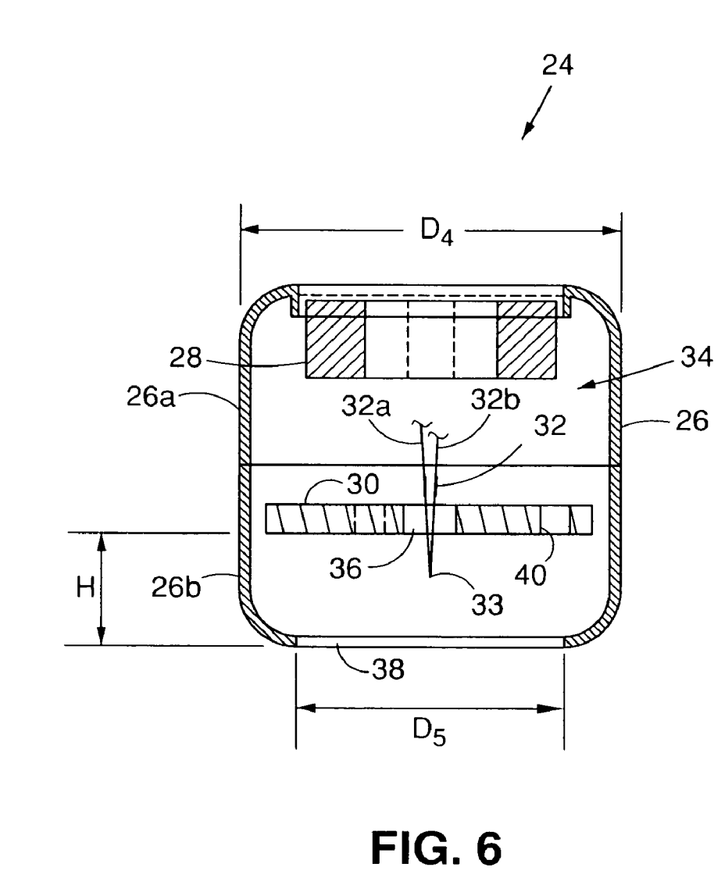
FIG. 6 is a schematic sectional view of the electron beam generator of FIG. 5.
Figure 7:
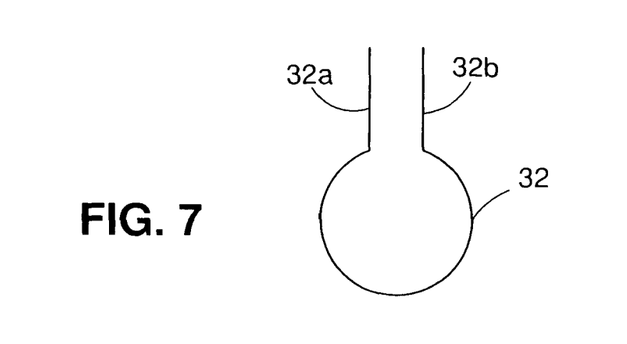
FIGS. 7-11 are schematic drawings of filaments having circular portions.
Figure 8:
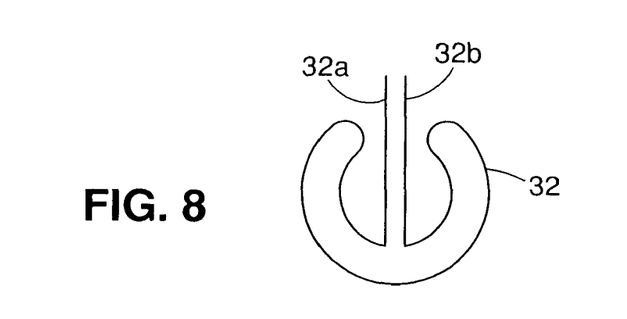
Figure 9:
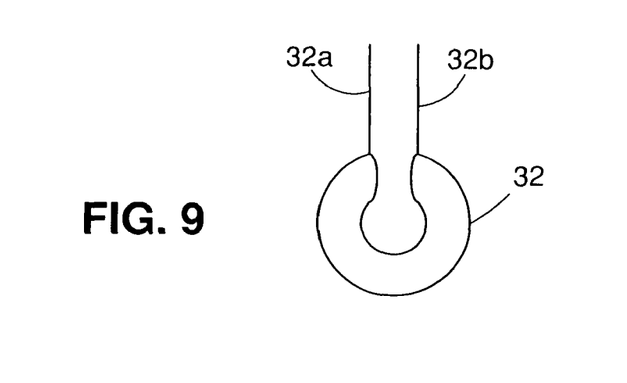
Figure 10:
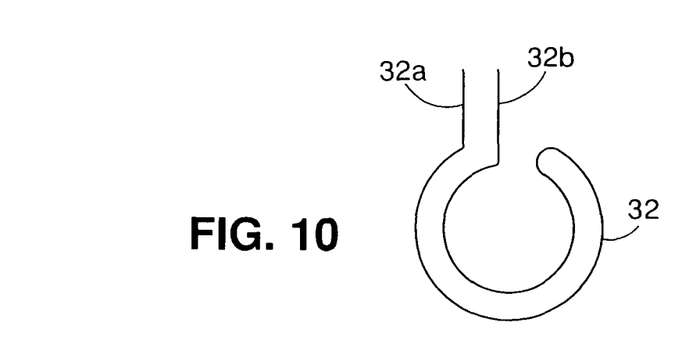
Figure 11:
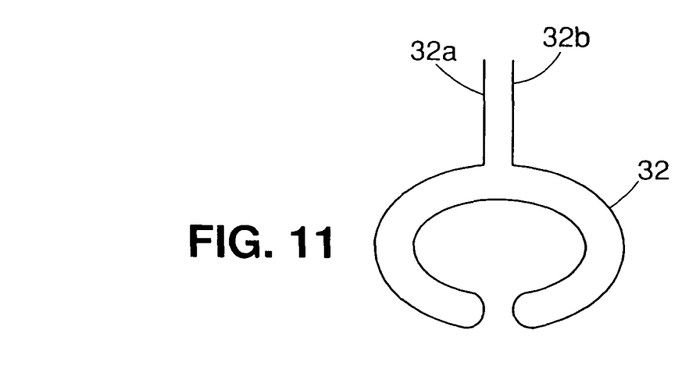

An electron gun or generator 24 for generating the electrons $e^-$ can be positioned within the interior 22 of the vacuum chamber 11, a distance $L_2$ from the axial proximal end of the nozzle 12, and a distance $L_3$ from exit window 42 at the axial distal end 14 of nozzle 12. The electron generator 24 can include a housing 26 which can be generally cylindrical in shape with a circular periphery, and can have a width or diameter $D_4$. The housing 26 can include two housing portions 26a and 26b which are joined together (FIGS. 5 and 6). The sides of the housing 26 can be spaced from the interior surfaces 11a of the vacuum chamber 11 by a distance of W which can provide a high voltage gap. An electron generating filament 32 can be positioned within the interior 34 of the housing 26. Power to the electron generating filament 32 can be provided from power source 13 through leads 32a and 32b, which can extend from housing 26 through an insulator 28. The electron generating filament 32 can have a portion that is longitudinally positioned in an orientation that is generally in line with the longitudinal axis "X" of the nozzle 12 and vacuum chamber 11 (FIG. 4). The electron generating filament 32 can have a slight V-shape (FIG. 6), with leads 32a and 32b extending from a distal end or point 33 at an angle from each other and towards the insulator 28. The electron generating filament 32 can generate free electrons $e^-$ when heated by electrical power passing through the filament 32. The general inline orientation of the electron generating filament 32 in electron generator 24 can provide electrons $e^-$ in a configuration, arrangement, or location, that is suitable for being focused, or shaped and conveyed or directed through the nozzle 12. The V-shape of the electron generating filament 32 can also provide electrons $e^-$ in a suitable configuration. The electron generating filament 32 can extend through an opening 36 in an electrostatic, focusing or shaping lens or member 30. The electrostatic lens 30 can provide initial focusing or shaping of the electrons $e^-$ and can have openings 40 for aiding in providing the desired focus. The axial end of the housing 26 can have an electron permeable or emitting region or opening 38 with a diameter $D_5$, through which the electrons $e^-$ from the filament 32 and electrostatic lens 30 pass, and which can form another electrostatic focusing or shaping lens or member for further focusing or shaping the electrons $e^-$ emitted from electron generator 24. High voltage potential can be provided between housing 26 of the electron generator 24 and the exit window 42 by power source 13. The exit window 42 can have a ground 48. The voltage potential between the electron generator 24 and the exit window 42 can accelerate the electrons e⁻ emitted by the electron generating filament 32, from the electron generator 24 towards and through the exit window 42. Although the electron generating filament 32 is typically longitudinally positioned, in some embodiments, the electron generating filament 32 can be laterally positioned. In addition, in some embodiments, multiple filaments 32 can be employed. Furthermore, the electron generating filament 32 can be a laterally or longitudinally positioned generally circular filament. Examples of some embodiments are depicted in FIGS. 7-11. FIGS. 8-11 depict examples where the filament 32 is bent to have a generally circular outer filament portion that substantially surrounds a generally circular inner filament portion.

The electron generator 24 can be positioned within the interior 22 of the vacuum chamber 11 and configured, shaped and dimensioned to form an internal narrow electron beam 46 of a shape and configuration that can travel through the nozzle 12 and emerge out the exit window 42 as electron beam 44. The configuration of the electrostatic lens 30, the diameter of the opening 36 in electrostatic lens 30, the distance H at which the electrostatic lens 30 is positioned from the opening 38, the diameter $D_5$ of the opening 38, and the orientation and configuration of filament 32, can be arranged or configured so that the electrons e⁻ exiting the electron generator 24 exit in a desired configuration. The internal electron beam 46 can exit the electron generator 24 in a manner that narrows or converges in a narrowing or converging portion 46a. The diameter $D_4$ of the housing 26 can be generally about the same diameter as the inner diameter $D_3$ of the nozzle 12, and the diameter $D_5$ of the opening 38 of the housing 26 can be smaller than the inner diameter $D_3$ of the nozzle 12. This can allow the converging portion 46a of the internal electron beam 46 to enter the narrow nozzle 12 with little or no blockage. The distance $L_2$ of the electron generator 24 can be also sufficiently spaced from the axial proximal end of the nozzle 12 to allow the converging portion 46a to enter. The internal electron beam 46 can converge at a convergence or focus point 46b within the nozzle 12, and then widen, diverge or spread out in a widening, spreading or diverging portion 46c before exiting the exit window 42 in a widening, spreading or diverging external electron beam 44. The electron beam 44 can direct electrons e⁻ away from the exit window 42 longitudinally along the longitudinal axis "X" as well as circumferentially radially outward relative to axis "X". The electron beam 44 can have an outwardly angled conelike shape. In some embodiments, the diameter $D_4$ of the housing 26 and the diameter $D_5$ of the opening 38 can be larger than the inner diameter $D_3$ of the nozzle 12. In such a situation, the electron generator 24 can be configured and spaced a sufficient distance $L_2$ to provide an internal electron beam 46 with a converging portion 46a that sufficiently narrows or converges to enter nozzle 12, and a diverging portion 46b that reaches the exit window 42.

The narrowing or converging, and then widening or diverging configuration of the internal electron beam 46 can keep the internal electron beam 46 narrow while within the nozzle 12 to allow travel of the beam 46 therethrough, and can allow the use of long narrow nozzles 12. For example, in some embodiments, the length $L_1$ to inner width or diameter $D_3$ ratio of the nozzle 12 can be at least about 3:1, for example about 6:1 or greater, and in other embodiments, about 10:1 or greater. In addition, the ratio of the width or diameter $D_1$ of the vacuum chamber 11 to the outer width or diameter $D_2$ of the nozzle 12 can be about 2:1, and in other embodiments about 3:1. Depending upon the application at hand, these ratios can vary. In some embodiments, the beam 46 can be formed in only a diverging manner, but may result in a shorter nozzle for a given inner diameter $D_3$, and can be about half as long. In some embodiments, the nozzle 12 can be tapered. The configuration of the electron generator 24, and distances $L_2$ and $L_3$, can be adjusted to provide the desired internal electron beam 46 configuration to enter a nozzle 12 of a given length $L_1$ an inner diameter $D_3$, and obtain a desired electron beam 44 configuration exiting the exit window 42. The nozzle 12 can have different lengths $L_1$, and outer widths or diameters $D_2$, for insertion into different sized containers or bottles 20. For example, different sized nozzles 12 can be employed for 12 oz. bottles 20 and 32 oz. or 2 liter bottles 20. For example, wider nozzles 12 can be used for wider bottles 20 with wider necks 16, and longer nozzles 12 can be used for taller bottles 12. In some embodiments, the same nozzle 12 can be used in a range of different sized containers of bottles 20.

The vacuum chamber 11 and nozzle 12 can be formed of metal, ceramics, or a combination thereof. In one embodiment, the vacuum chamber 11 can have a width or diameter of about 2 inches. Vacuum chamber 11 can have larger or smaller widths and diameters depending upon the application at hand and the desired power levels. The housing 26 of the electron generator 24 can be formed of conductive material, for example metal, such as stainless steel. Filament 32 can be formed of a suitable material such as tungsten. The electron beam emitter 10 can be operated in a range between about 40 to 150 KV, and about 0 to 5 milliAmps. Alternatively, higher or lower voltages can also be used. It is understood that dimensions and voltage and power levels can vary depending upon the application at hand. Some features of the electron beam emitter 10 can be similar to embodiments disclosed in U.S. Pat. Nos. 5,962,995, 6,407,492, and 6,545,398, the contents of which are incorporated herein by reference in their entirety.

The exit window 42 can extend across substantially the width of the inner diameter $D_3$ of the nozzle 12 at the axial distal end 14. The exit window 42 can be formed of suitable materials, for example, titanium having a thickness of 12.5 microns or less. In some embodiments, the thickness can be between about 4-12 microns thick. Other embodiments can have larger or smaller thicknesses. The exit window 42 can have a corrosion resistant covering, for example, gold, diamond, etc. The exit window 42 can be sealed or bonded to the nozzle 12 to preserve a hermetically sealed vacuum with nozzle 12 and vacuum chamber 11. A support plate with holes therethrough can be used to support the exit window 42. Other suitable materials and configurations can be employed for exit window 42. Exit window 42 can include constructions disclosed in U.S. application Ser. No. 10/751,676, filed Jan. 5, 2004, the contents of which are incorporated herein by reference in its entirety. In some embodiments, a support plate can be omitted. In addition, the exit window 42 can be formed of corrosion resistant material without a layer of titanium.

In another embodiment, the exit window 42 can be a target window being made of a material and having a thickness sufficient to substantially prevent the passage of electrons e⁻ through from the internal electron beam 46 while forming and allowing the forward passage of x-rays, thereby providing an x-ray beam emitter for emitting forward x-ray beams through a narrow nozzle 12. The target window can include a thin foil of gold, titanium, or tungsten, or titanium having a layer of gold, or gold with copper or silver. Typically, metals with a high Z number and good thermal conductivity are employed, but materials can vary depending upon the situation at hand.

While this invention has been particularly shown and described with references to example embodiments thereof, it will be understood by those skilled in the art that various changes in form and details may be made therein without departing from the scope of the invention encompassed by the appended claims.

For example, although the vacuum chamber 11 and nozzle 12 have been described to have generally circular peripheries, in other embodiments, the peripheries can be of other suitable shapes, for example, polygonal, such as triangular, rectangular, square, hexagonal, octagonal, etc., or non-circular curves for example, oval, egg shaped, etc. In some embodiments, the electron beam emitter 10 can be used for irradiating the interior of containers and bottles for purposes other than sterilization, or neutralization for example, for curing, surface treatment, etc.

What is claimed is:

1. An electron beam emitter for sterilizing containers comprising:
    a vacuum chamber having a width;
    an electron generator positioned within the vacuum chamber for generating electrons; and
    an elongate nozzle extending from the vacuum chamber along a longitudinal axis and having an exit window at a distal end of the nozzle, the nozzle having a width that is less than the width of the vacuum chamber, the electron generator being shaped and dimensioned, and positioned within the vacuum chamber to form and direct a narrow electron beam that enters and travels through the nozzle, and exits out the exit window, the electron generator including a housing, the electron beam exiting the housing of the electron beam generator in a narrowing manner, whereby an initial focusing lens is positioned within the housing for providing initial focusing of the electrons within the housing, and the housing having an axial end with an opening shaped for forming a second lens for providing further progressive focusing of the electrons as the electron beam exits the housing of the electron generator.

2. The emitter of claim 1 in which the nozzle has a generally circular periphery, and has a diameter.

3. The emitter of claim 2 in which the vacuum chamber has a generally circular periphery, and has a diameter that is larger than the diameter of the nozzle.

4. The emitter of claim 2 in which the nozzle has a length, and a length to diameter ratio of at least about 3:1.

5. The emitter of claim 3 in which the electron generator has a housing with a diameter that is about the same as the diameter of the nozzle.

6. The emitter of claim 3 in which emitter has a vacuum chamber diameter to nozzle diameter ratio of at least about 2:1.

7. The emitter of claim 1 in which the electron generator is shaped and dimensioned, and positioned to form the electron beam with a converging portion that converges within the nozzle, followed by a diverging portion that diverges within the nozzle before reaching the exit window.

8. The emitter of claim 7 in which the electron beam further diverges after exiting the exit window.

9. The emitter of claim 1 in which the electron generator includes an electron generating filament having a portion that is oriented generally longitudinally in line with the longitudinal axis of the nozzle.

10. A method of generating an electron beam for sterilizing containers comprising:
    generating electrons with an electron generator positioned within a vacuum chamber, the vacuum chamber having a width;
    extending an elongate nozzle from the vacuum chamber along a longitudinal axis, the nozzle having an exit window at a distal end of the nozzle, the nozzle having a width that is less than the width of the vacuum chamber; and
    shaping and dimensioning, and positioning the electron generator within the vacuum chamber to form and direct a narrow electron beam that enters and travels through the nozzle, and exits out the exit window, the electron generator including a housing, the electron beam exiting the housing of the electron beam generator in a narrowing manner, whereby an initial focusing lens is positioned within the housing for providing initial focusing of the electrons within the housing, and the housing having an axial end with an opening shaped for forming a second lens for providing further progressive focusing of the electrons as the electron beam exits the housing of the electron generator.

11. The method of claim 10 further comprising providing the nozzle with a generally circular periphery, and a diameter.

12. The method of claim 11 further comprising providing the vacuum chamber with a generally circular periphery, and a diameter that is larger than the diameter of the nozzle.

13. The method of claim 11 further comprising providing the nozzle with a length, and a length to diameter ratio of at least about 3:1.

14. The method of claim 12 further comprising providing the electron generator with a housing having a diameter that is about the same as the diameter of the nozzle.

15. The method of claim 12, further comprising providing a vacuum chamber diameter to nozzle diameter ratio of at least about 2:1.

16. The method of claim 10 further comprising shaping and dimensioning, and positioning the electron generator to form the electron beam with a converging portion that converges within the nozzle, followed by a diverging portion that diverges within the nozzle before reaching the exit window.

17. The method of claim 16 further comprising diverging the electron beam after exiting the exit window.

18. The method of claim 10 in which the electron generator includes an electron generating filament, the method further comprising orienting a portion of the filament generally longitudinally in line with the longitudinal axis of the nozzle.

19. A method of irradiating an interior of a bottle for sterilizing, the bottle having a neck, the method comprising:
    generating electrons with an electron generator positioned within a vacuum chamber, the vacuum chamber having a width;
    extending an elongate nozzle from the vacuum chamber along a longitudinal axis, the nozzle having an exit window at a distal end of the nozzle, the nozzle having a width that is less than the width of the vacuum chamber;
    shaping and dimensioning, and positioning the electron generator within the vacuum chamber to form and direct a narrow electron beam that enters and travels through the nozzle, and exits out the exit window, the electron generator including a housing, the electron beam exiting the housing of the electron beam generator in a narrowing manner, whereby an initial focusing lens is positioned within the housing for providing initial focusing of the electrons within the housing, and the housing having an axial end with an opening shaped for forming a second lens for providing further progressive focusing of the electrons as the electron beam exits the housing of the electron generator; and inserting the nozzle through the neck of the bottle and irradiating the interior with the electron beam.

20. The method of claim 19 further comprising providing the elongate nozzle with a generally circular periphery, and a diameter.

21. The method of claim 20 further comprising providing the vacuum chamber with a generally circular periphery, and a diameter that is larger than the diameter of the nozzle.

22. The method of claim 20 further comprising providing the nozzle with a length, and a length to diameter ratio of at least about 3:1.

23. The method of claim 21 further comprising providing the electron generator with a housing having a diameter that is about the same as the diameter of the nozzle.

24. The method of claim 21 further comprising providing a vacuum chamber diameter to nozzle diameter ratio of at least about 2:1.

25. The method of claim 19 further comprising shaping and dimensioning, and positioning the electron generator to form the electron beam with a converging portion that converges within the nozzle, followed by a diverging portion that diverges within the nozzle before reaching the exit window.

26. The method of claim 25 further comprising diverging the electron beam after exiting the exit window.

27. The method of claim 19 in which the electron generator includes an electron generating filament, the method further comprising orienting a portion of the filament generally longitudinally in line with the longitudinal axis of the nozzle.

28. The method of claim 19 further comprising moving the bottle and the nozzle relative to each other during irradiation.

29. The method of claim 19 further comprising assisting the distribution of the electron beam within the interior of the bottle with at least one electron directing member adjacent to the bottle.

30. The method of claim 19 in which interior of the bottle has an ambient gaseous environment, the method further comprising modifying the gaseous environment within the bottle.

* * * * *